(12) United States Patent
Shapiro et al.

(10) Patent No.: US 6,436,139 B1
(45) Date of Patent: Aug. 20, 2002

(54) INTERBODY FUSION DEVICE WITH ANTI-ROTATION FEATURES

(75) Inventors: David E. Shapiro, Highland Park, IL (US); Thomas Victor McGahan, Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/498,050

(22) Filed: Feb. 4, 2000

Related U.S. Application Data

(60) Provisional application No. 60/118,939, filed on Feb. 4, 1999.

(51) Int. Cl.[7] .................................................. A61F 2/44
(52) U.S. Cl. ................................................... 623/17.11
(58) Field of Search ........................... 623/17.11, 17.12, 623/17.16; 606/61

(56) References Cited

U.S. PATENT DOCUMENTS

| | | | |
|---|---|---|---|
| 5,015,247 A | 5/1991 | Michelson | 606/61 |
| 5,458,638 A | 10/1995 | Kuslich et al. | 623/17 |
| 5,593,409 A | 1/1997 | Michelson | 606/61 |
| 5,609,636 A | 3/1997 | Kohrs et al. | 623/17 |
| 5,645,598 A | 7/1997 | Brosnahan, III | 623/17 |
| 5,669,909 A | 9/1997 | Zdeblick et al. | 606/61 |
| 5,683,463 A | 11/1997 | Godefroy et al. | 623/17 |
| 5,709,683 A | 1/1998 | Bagby | 606/61 |
| 5,766,252 A | 6/1998 | Henry et al. | 623/17 |
| 5,865,845 A | 2/1999 | Thalgott | 623/17 |
| 5,865,847 A | 2/1999 | Kohrs et al. | 623/17 |
| 5,885,287 A | 3/1999 | Bagby | 606/61 |
| 5,904,719 A | 5/1999 | Errico et al. | 623/17 |
| 5,906,616 A | 5/1999 | Pavlov et al. | 606/61 |
| 5,947,971 A | 9/1999 | Kuslich et al. | 606/80 |
| 6,168,631 B1 * | 1/2001 | Maxwell et al. | 623/17.11 |

FOREIGN PATENT DOCUMENTS

| | | | |
|---|---|---|---|
| EP | 0 637 440 A1 | 8/1994 | A61F/2/44 |
| EP | 0716 840 A2 | 12/1995 | A61F/2/44 |
| WO | WO 96/40020 | 12/1996 | A61F/5/04 |
| WO | WO 98/38924 A3 | 9/1998 | |
| WO | WO 98/38924 A2 | 9/1998 | |

* cited by examiner

*Primary Examiner*—Bruce Snow
*Assistant Examiner*—Brian E. Pellegrino
(74) *Attorney, Agent, or Firm*—Woodard, Emhardt, Naughton Moriarty & McNett

(57) ABSTRACT

An improved interbody fusion device incorporating anti-rotation features to inhibit accidental screwing or unscrewing of the fusion device in an intervertebral disc space. One such feature is a thread pattern having a crest diameter that increasingly tapers from a smaller diameter at the insertion end to a larger diameter at the opposite end making further advancement of the thread into the bone more difficult. Another feature is a thread cut out on the trailing edge of the thread, creating a barb which has a tendency to inhibit unscrewing. These features may be used alone or in combination for an improved interbody fusion device.

18 Claims, 11 Drawing Sheets

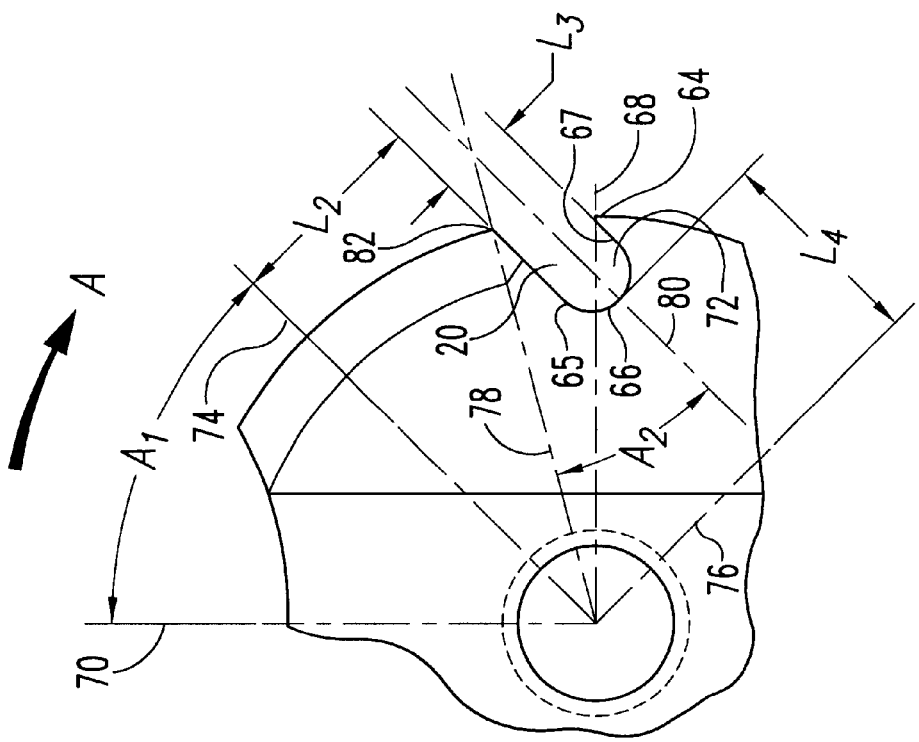
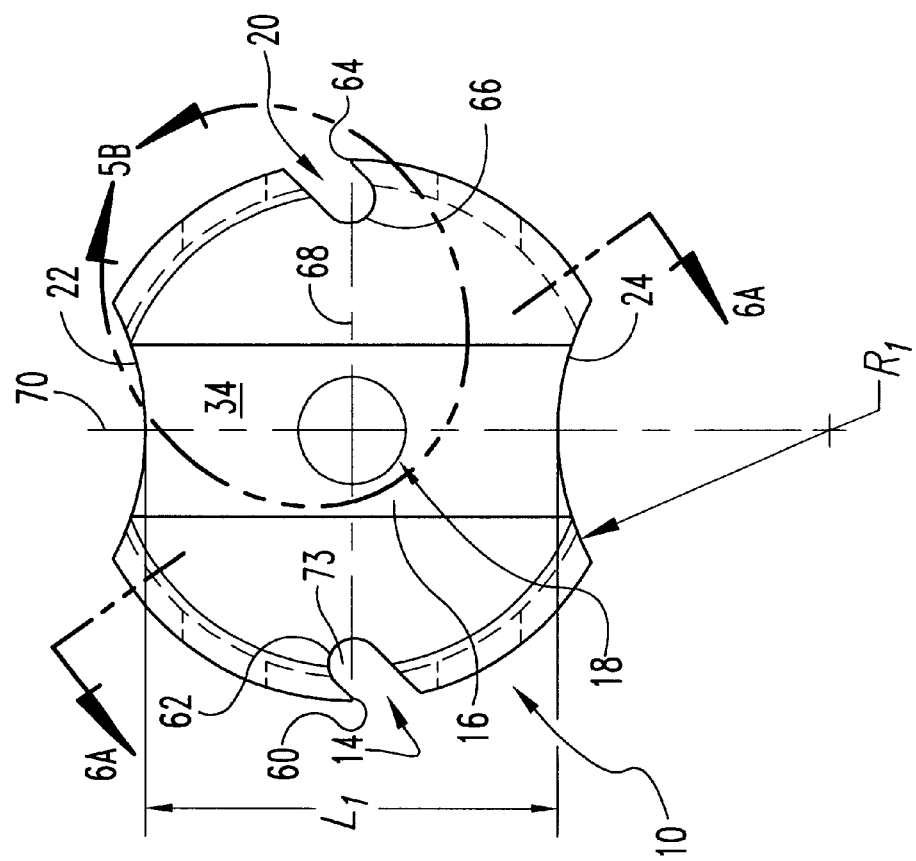
Fig. 5B
Fig. 5A

INTERBODY FUSION DEVICE WITH ANTI-ROTATION FEATURES

The present application claims the benefit of the filing date of Provisional application Serial No. 60/118,939, filed Feb. 4, 1999, entitled IMPROVED INTERBODY FUSION DEVICE WITH ANTI-ROTATION FEATURES. The referenced application is incorporated herein by reference in its entirety.

BACKGROUND OF THE INVENTION

The present invention relates to interbody fusion devices disposed between two bony structures to maintain spacing therebetween and promote bony fusion. More specifically, the present invention relates to interbody fusion devices having threads or other structures defined on the outer surface to limit movement of the device between the bony structures. Most often, such devices find application in the spine for fusing adjacent vertebrae.

It is well known to utilize an artificial spinal fusion implant to be inserted in the space between two adjacent vertebra after removal of a damaged spinal disc or portion thereof. Common forms of such devices may be configured in a substantially cylindrical configuration. These cylindrical configurations can include truncated sidewalls or a tapering body portion. However, for bone fusion to occur, the invasion of new delicate blood vessels from the adjacent healthy bone is necessary for the creation of new living interconnecting bone. Motion around the implant can restrict or even prevent bone healing. Therefore, it is important to stabilize the implant upon insertion. In most applications, the outer body of the fusion device is provided with one or more structures to resist repulsion from the disc space when a load is applied to the spinal column. For example, U.S. Pat. No. 5,015,247 issued to Michelson discloses substantially cylindrical interbody fusion devices with an external thread disposed on the outer surface. The thread is interrupted at various locations. Further, the trailing portion of the thread may be twisted slightly. This twisted portion of the trailing edge acts as a locking thread to resist subsequent unscrewing of the fusion device. While such interrupted locking threads may be satisfactory in preventing unscrewing, the manufacturing process of twisting each of the individual teeth to create a locking thread may be costly and difficult to control from a quality aspect.

Thus, there remains a need for an improved interbody fusion device that incorporates features to resist undesired rotation after implantation while at the same time simplifying the insertion of the implant into a human body and minimizing manufacturing complexity.

SUMMARY OF THE INVENTION

The present invention provides an interbody fusion device having structures to limit rotation in at least one direction after the device is implanted between two bony structures. In one aspect of the present invention, an improved interbody fusion device is provided with an anti-rotation thread cut out. In this aspect, the fusion device includes a body portion with a thread pattern defined thereon. The thread pattern extends at least partially from a first end to an opposite second end. At least one thread is interrupted by a thread cut out on a trailing edge of the thread. The thread cut out includes an undercut portion extending beneath the outer surface of the interrupted thread to create a barb. When force is applied, attempting to unscrew the device, material from the thread path may be urged into the undercut area and retained there to resist accidental unscrewing. Preferably, the thread cut out also creates a relatively sharp pointed barb. The pointed barb may tend to impale bone tissue, further increasing resistance to unscrewing.

In a further aspect, the invention provides an interbody fusion device with an outer surface extending between a first end an opposite second end. A thread pattern is defined on the outer surface and extends at least partially between the first and second ends. A first thread adjacent the first end has a first height and a second thread adjacent the second end has a second larger height. The height of intervening threads between the first and second threads includes a substantially continuously tapering height increasing from said first thread to said second thread. In a preferred aspect, the outer surface of the fusion device has a substantially continuous outer diameter. When inserted into the disc space with the first end leading the insertion, the first thread travels through a thread path and each subsequent larger thread expands the thread path by engaging bone not contacted by the preceding thread. In this manner, resistance to further screwing of the device into the disc space is increased. Thus, the expanding thread pattern resists accidental movement of the device into the disc space as a result of further rotation.

In yet a further preferred aspect of the present invention, an interbody fusion device is provided incorporating both a thread pattern having a cut out on the trailing surface of the thread to resist accidental unscrewing and a tapering thread height to resist accidental advancing. This combination provides an improved interbody fusion device resistant to accidental rotation after implantation.

These and other objects of the present invention will be apparent from the following description of the preferred embodiments.

BRIEF DESCRIPTION OF THE DRAWINGS

FIG. 5A is an end view of the interbody fusion device of FIG. 4A.

FIG. 5B is an enlarged end view of a portion of FIG. 5A.

DESCRIPTION OF THE PREFERRED EMBODIMENTS

Figure 1:
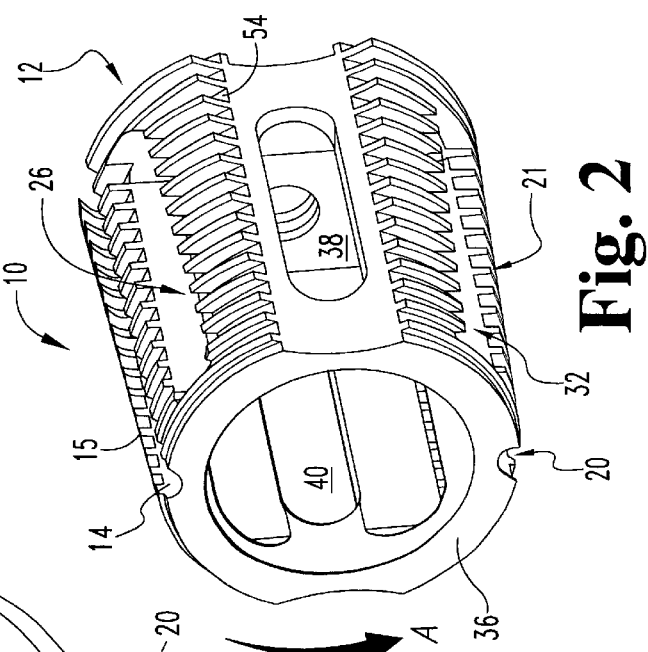
FIG. 1 is a perspective view of an improved interbody fusion device according to the present invention.
Figure 2:
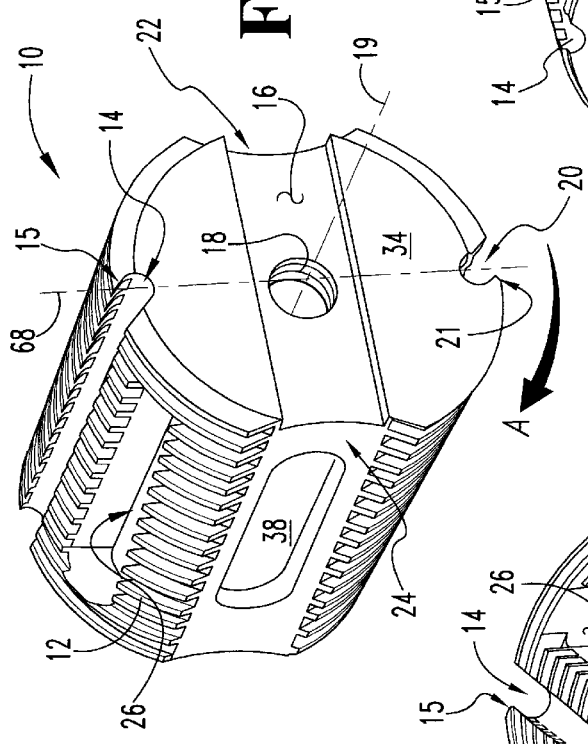
FIG. 2 is a second perspective view of the interbody fusion device of FIG. 1.
Figure 3:
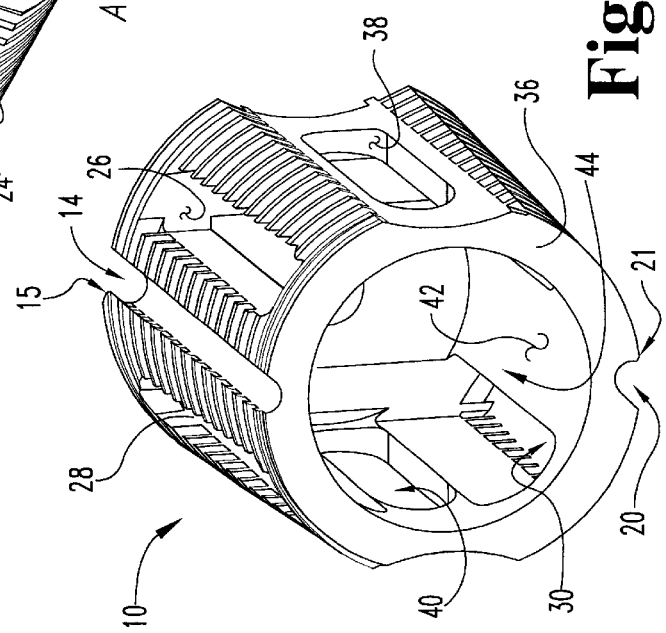
FIG. 3 is a third perspective view of the interbody fusion device of FIG. 1.
Figure 4A:
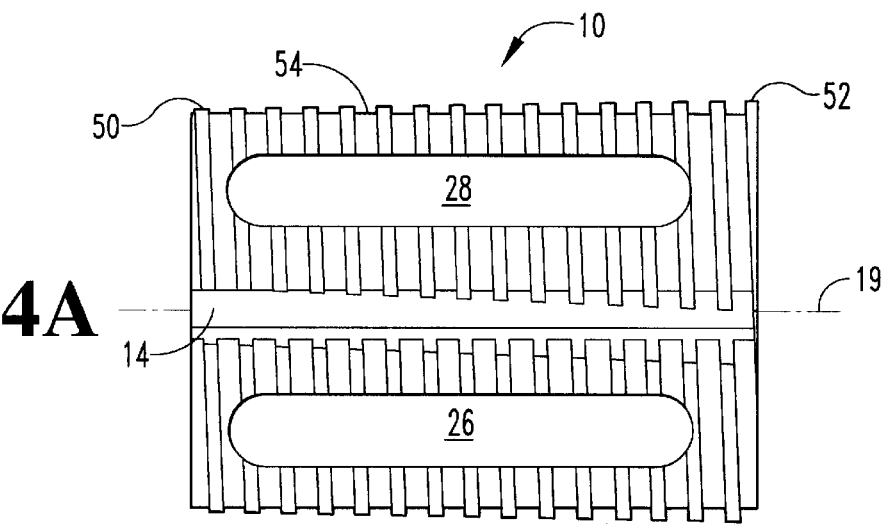
FIG. 4A is a top view of the interbody fusion device of FIG. 1.
Figure 4B:
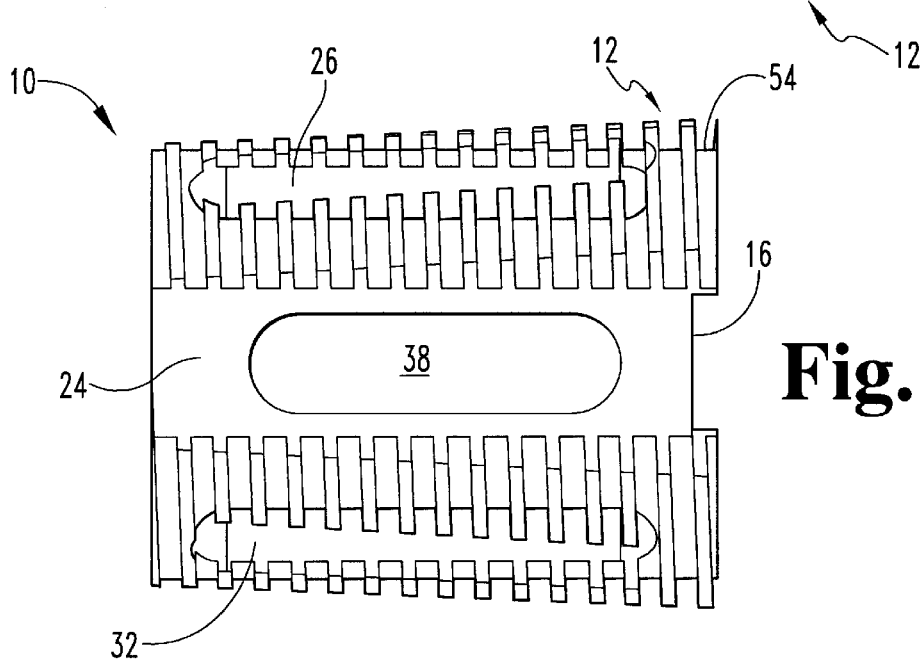
FIG. 4B is a side view of the interbody fusion device of FIG. 1.
Figure 4C:
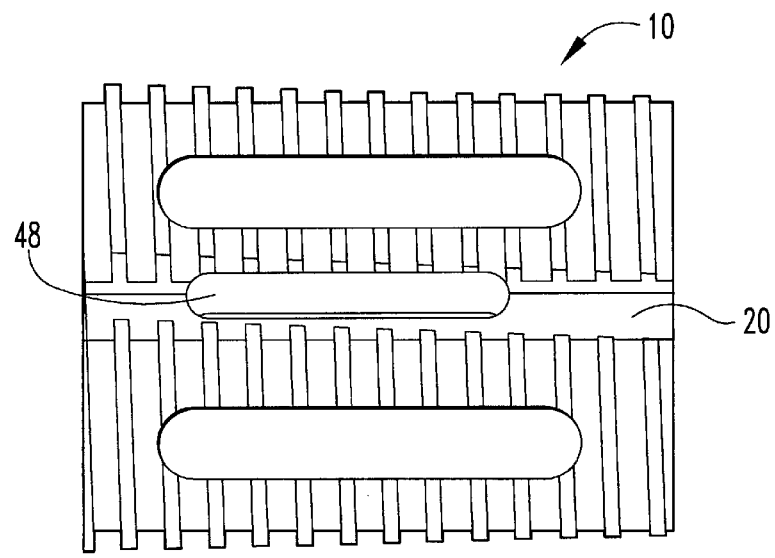
FIG. 4C is a top view of an-alternative embodiment according to the interbody fusion device of FIG. 1.
Figure 5C:
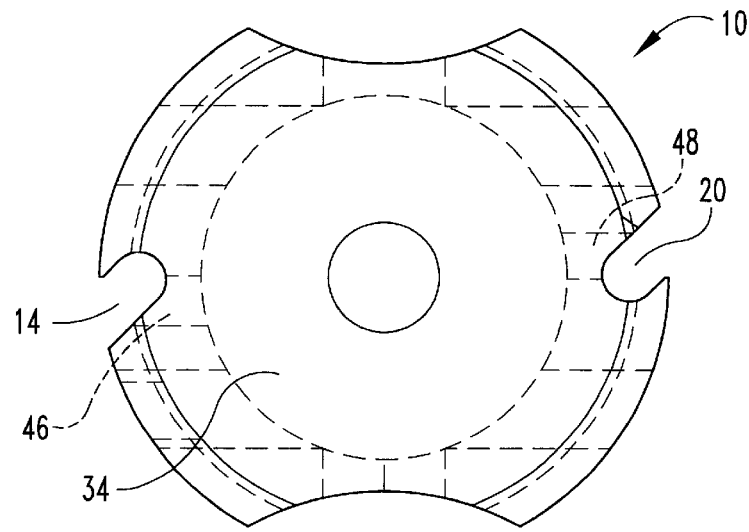
FIG. 5C is an end view of the interbody fusion device of FIG. 4C.

For the purposes of promoting an understanding of the principles of the invention, reference will now be made to the embodiments illustrated in the drawings and specific language will be used to describe the same. It will nevertheless be understood that no limitation of the scope of the invention is thereby intended, and such alterations and further modifications in the illustrated device, and such further applications of the principles of the invention as illustrated therein being contemplated as would normally occur to one skilled in the art to which the invention relates.

Referring now to FIGS. 1 through 6, there is shown an improved interbody fusion device or cage 10 according to the present invention. Device 10 comprises an elongated body having an outer surface 54 extended between a first end 34 and a second end 36 and defining a longitudinal axis 19. End 34 is referred to as the proximal end since it is the end closest to the user as the device is being inserted into a vertebral disc space. A helical thread pattern 12 is formed on outer surface 54, having an advancing rotation direction shown by arrow A for inserting device 10 into a disc space. Thread pattern 12 is interrupted by thread cut outs 14 and 20, multiple bone ingrowth or fusion windows 26, 28, 30 and 32, and opposing sidewalls 22 and 24.

Interbody fusion device or implant or spacer 10 further includes an inner surface 42 defining a hollow interior chamber 44 adapted to receive bone growth promoting material to promote fusion between adjacent vertebral bodies. As known in the art, hollow chamber 44 may be sealed by a cap (not shown) placed over the opening adjacent distal end 36.

The fusion device further includes driving slot 16 and internally threaded opening 18 adapted to receiving an insertion tool (not shown). Preferably, the insertion tool has a driving shoulder to engage driving slot 16 and an externally threaded shaft adapted for engagement with internally threaded opening 18.

The interbody fusion devices, or implant or spacer 10 are commonly sized in diameters ranging from 16 mm to 20 mm and in lengths ranging from 20 mm to 23 mm, although other sizes of the interbody fusion devices are contemplated depending on the requirements of a given medical indication. A preferred embodiment having a diameter of approximately 18 mm is being illustrated.

Referring to FIGS. 1, 3, 5A, and 5B, two substantially identical thread cut outs 14 and 20 interrupt thread pattern 12 on diametrically opposing sides along transverse axis 68 of fusion device 10. While two thread cut outs are shown in a preferred embodiment, it is contemplated that a greater or lesser number of thread cut outs may be utilized without deviating from the spirit and scope of the invention. Further, while thread cut outs are shown extending along substantially the entire length of device 10 from a first end 34 to a second end 36 and parallel to longitudinal axis 19, it is contemplated that the thread cut outs 14, 20 may be formed in a single thread turn or form or in alternating positions. As shown in FIG. 1, the thread cut outs form a series of barbs 15 and 21 on the trailing edge of the thread form. The trailing edge of the thread refers to the back side of the thread as it threadedly advances into the vertebral bodies. Due to the elastic nature of cancellous bone, a portion of the cancellous bone often springs back into the open thread path left in the area of the thread cut outs. This also occurs to a much greater extent during the healing process following insertion. Thus, after insertion the thread cut outs will be at least partially filled with bone.

Thread cutouts 14 and 20 are formed by cutting into the extending thread forms of thread pattern 12 at a predetermined angle to a predetermined depth with a cutting instrument having specified width or diameter. Preferably, each of the thread cut outs 14 and 20 includes a base portion 62 and 66, a barb or protrusion 60 and 64, leading wall 65 and trailing wall 67. Barbs or overhanging thread portions 60 and 64 resemble a shark's dorsal fin. As shown more clearly in FIG. 5B, base portion 66 and overhanging thread portion 64 define a recess or undercut 72. In a preferred embodiment, undercut 72 is substantially concave. Further, extending thread crest of barb 64 forms a relatively sharp point with trailing wall 67 of cut out 20. Barbs 60 and 64, in combination with recess 72 and a corresponding recess 73 in cut out 14, respectively, encourage material from the thread path to be trapped within the concave area thereby inhibiting unscrewing of the device through the previous thread path. Further, the sharp points of fin-shaped barbs 60 and 64 face away from the threadedly advancing rotation direction. In the forward insertion direction, barbs 60 and 64 have little impact on the rotational motion. In the reverse, backward direction, barbs 60 and 64 tend to impale the adjacent bones or matters which collected in the thread path, thus resisting reverse rotation of the device 10.

Referring again more specifically to FIG. 5B, thread cut out 20 is formed in a preferred aspect of the invention by forming a cut into thread pattern 12 at an angular orientation A1 with respect to axis 70 along the rotation direction A. It is contemplated that this angle may range from 0° to less than 90°. In a preferred embodiment, angle A1 is approximately 45°. The leading wall 65 of cut out 20 is spaced from imaginary line 74 by a distance L2 and extends at angle A1 with respect to axis 70. In a preferred embodiment of a fusion device having a maximum diameter of 18 mm, L2 is equal to approximately 4.6 mm. Thread cut out 20 has a width extending between leading wall 65 and trailing wall 67 of L3. In a preferred embodiment, L3 is approximately 1.75 mm. Thus, the ratio of the width or diameter of the thread cut out 20 to the diameter of device 10 is approximately 10%. However, it will be understood that this ratio may be as high as 50% or as low as single digit percentages. Further, the thread cut out extends to a depth of L4 from imaginary line 76, which is perpendicular to imaginary line 74. In a preferred embodiment, L4 is approximately 4.7 mm. In further explanation of the features disclosed in FIGS. 5A and 5B, the centerline 80 of the thread cut out 20 is disposed at angle A2 with respect to a ray 78 extending from the center to the intersection 82 of thread cut out 20 and thread form. It is contemplated that this angle may be less than 90° but greater than 0° to achieve a thread cut out according to the present invention. In the embodiment of FIG. 5B, angle A2 is approximately 30°. Preferably, as shown in FIG. 5B, a ray 68 connects thread overhang 64 with the center of the device 10. Trailing wall 67 is offset with respect to ray 68 to thereby define recess 72.

In one embodiment of the present invention, thread cut outs 14 and 20 extend into, but not through, the body of fusion device 10. In another embodiment, the cut out may extend only through the threads without disrupting the root diameter of the device. Yet in still another embodiment, referring to FIGS. 4C and 5C, the cut outs extend through the body wall to form bone ingrowth windows or openings 46 and 48. The bone ingrowth windows 46 and 48 permit bone ingrowth between bone growth promoting material placed in hollow interior 44 of the device and the adjacent bone of the vertebral bodies. The windows may also allow bone material, which may collect in the cutout as the device or implant 10 is being advanced, to fall into interior chamber 44. Further, while dimensions have been given for a specific and preferred embodiment having a maximum diameter of 18 mm, it is contemplated and understood that it will be readily apparent to those skilled in the art that other dimensions, angles, radii, etc., may be utilized without deviating from the spirit, scope and content of the present invention.

Thread pattern 12 is further interrupted by upper bone ingrowth windows 26 and 28 and opposing lower bone ingrowth windows 30 and 32. It will be understood that these bone ingrowth windows are disposed on the body of fusion device 10 such that, when implanted in a disc space, they are positioned adjacent the upper and lower vertebral bodies, respectively. The windows permit bone ingrowth between bone growth promoting material placed in hollow interior 44 of the device and the adjacent bone of the vertebral bodies.

The fusion device further includes concave sidewall 22 and opposing concave sidewall 24. The concave sidewall permits placement of two interbody fusion devices in a disc space that would otherwise not be able to receive two cylindrical interbody fusion devices due to their greater width. In a preferred embodiment, the fusion device 10 includes concave sidewall 22 and opposing concave sidewall 24, each extending along the length of the device.

Referring now to FIGS. 5A and 5B, concave sidewalls 22 and 24 are more clearly shown on diametrically opposed sides of device 10 along transverse axis 70. Concave sidewalls 22 and 24 are identically formed in mirror image. Concave sidewall 24 has a radius of curvature R1 approximating the external diameter of the interbody fusion device. Thus, with a fusion device 10 placed in the disc space with side walls 22 and 24 disposed laterally, an identically sized fusion device 10 may then be rotated into position with thread pattern 12 rotating within the concave area of the adjacent fusion device 10. For instance, for an 18 mm diameter cage, R1 equals 9.25 mm.

In the illustrated embodiment, each of the concave sidewall 22 and 24 is interrupted by lateral bone ingrowth windows 38 and 40, respectively. These lateral bone ingrowth windows 38 and 40 also permit communication between bone growth material placed within the interior of the device and fusion material placed around the exterior of the device in the disc space.

Figure 6A:
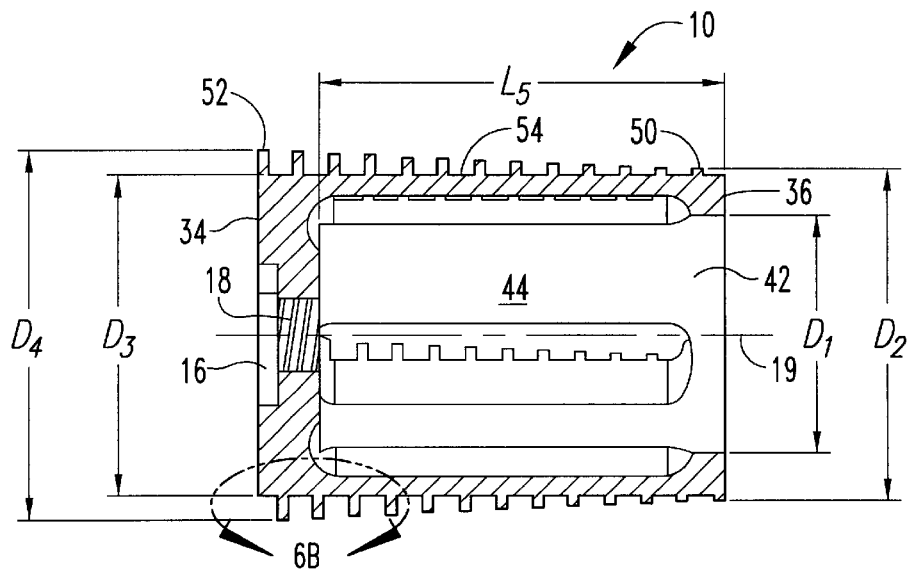
FIG. 6A is a cross-sectional view taken along line 6A—6A of FIG. 5A.
Figure 6B:
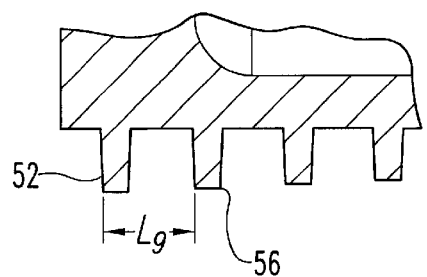
FIG. 6B is an enlarged view of a portion of FIG. 6A.

Referring now to FIG. 6A, there is shown a cross-sectional view of device 10 taken along line 6A—6A of FIG. 5A. Inner surface 42 has a diameter D1 which defines interior chamber 44. First thread revolution or turn or form 50 adjacent distal end 36 has a maximum thread crest diameter of D2. Outer surface 54 has a constant diameter D3 extending from distal end 36 to proximal end 34. The last thread turn 52 adjacent proximal end 34 has a maximum thread crest diameter D4 which is preferably slightly larger than D2. While these dimensions may vary depending on the size of the device and the specific design criteria, in a preferred embodiment for an 18 mm maximum diameter interbody fusion device, D1 is equal to approximately 11.5 mm, D2 is equal to approximately 16 mm, D3 is equal to approximately 15.5 mm, and D4 is equal to approximately 18 mm. Thus, it will be understood that the outer surface 54 has a constant cylindrical diameter of approximately 15.5 mm, thereby giving the thread pattern 12 a constant root diameter along outer surface 54. Thread pattern 12 increasingly tapers from a height of approximately 0.5 mm adjacent distal end 36 by substantially continuously increasing the height of each successive thread turn until it reaches its maximum height at last thread turn 52 adjacent proximal end 34. At this point, thread turn 52 has a height of 2.5 mm above surface 54. In a preferred embodiment, referring to FIG. 6B, thread turn 52 is separated from thread turn 56 by a distance of L9. Preferably distance L9 represents a 1.8 pitch for the thread pattern. The continuously expanding tapered thread pattern insures that upon each device revolution, the next greater height thread is engaging bone that has not been previously engaged or compressed by the preceding threads. The tapering thread pattern thereby resists further screwing of the device. While tapering the height of each successive thread turn is shown, the width of each successive thread may alternatively, or in combination with thread height, be increased to generate resistance to further screwing.

Figure 7:
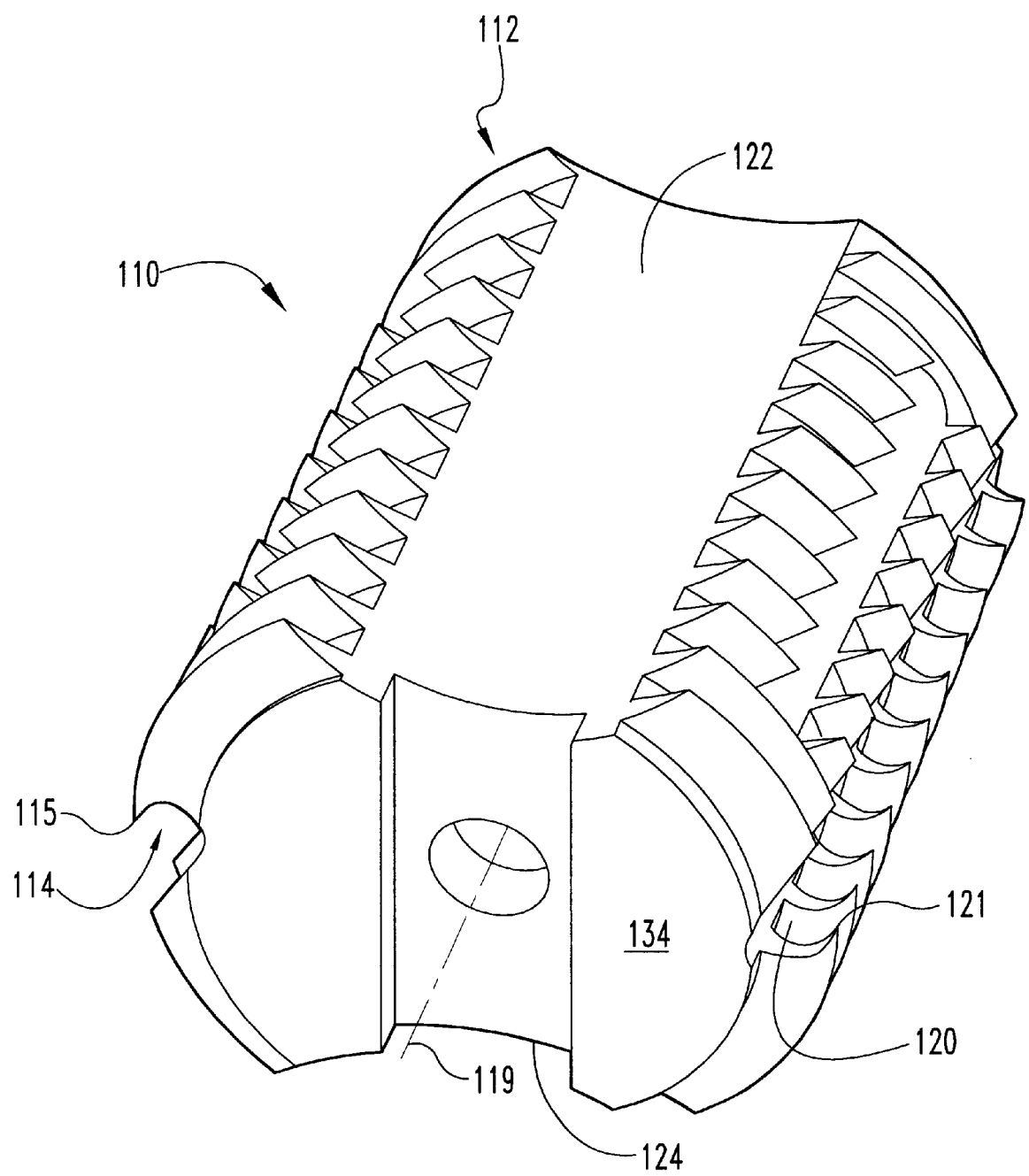
FIG. 7 is a perspective view of a further embodiment of an improved interbody fusion device according to the present invention.

Referring to FIG. 7, there is shown a second embodiment of the fusion device 110 of the present invention. Fusion device 110 includes a thread pattern 112 interrupted by thread cut outs 114 and 120. Thread cut outs 114 and 120 are configured substantially as shown with respect to the embodiment of FIG. 1 to create barbs 115 and 121. The longitudinally extending cut outs create a longitudinally extending series of such barbs substantially parallel to axis 119. Further, fusion device 110 includes opposing concave sidewalls 122 and 124. Moreover, the thread pattern is substantially tapering from a smaller thread form opposite end 134 to a larger thread form adjacent end 134. Fusion device 110 differs from fusion device 10 primarily in the fact that concave sidewalls 122 and 124 are substantially solid.

Figure 8:
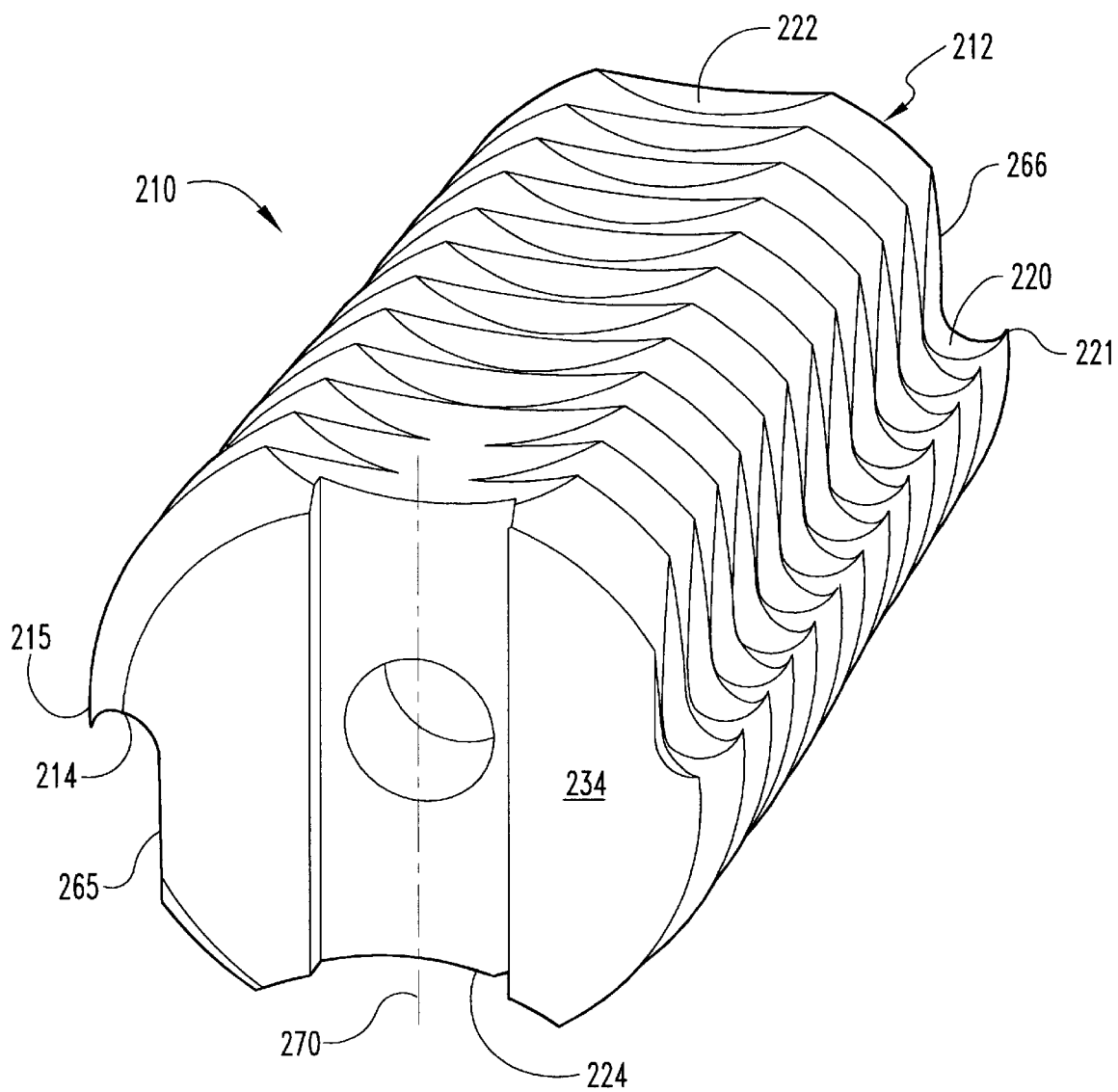
FIG. 8 is a perspective view of a third embodiment of an improved interbody fusion device according to the present invention.

Referring now to FIG. 8, there is shown yet a further embodiment of an improved interbody fusion device 210 according to the present invention. Fusion device 210 includes an external thread pattern 212 having a substantially continuous thread crest diameter. Thread pattern 212 is interrupted by thread cut outs 214 and 220 configured substantially as shown in FIG. 5A to form barbs 215 and 221, respectively. However, thread cut outs 214 and 220 differ in that the angle of the thread cut out with respect to the axis to 270 is substantially parallel rather than set at a 45° angle as shown in FIG. 5B. Thus, walls 265 and 266 are substantially parallel to axis 270. The thread cut out continues to have the undercut area to constrain material in the thread path. Further, the embodiment of FIG. 8 includes concave sidewalls 222 and 224. The depth of concave side walls 222 and 224 extends to a lesser extent into the body of fusion device 212 thereby retaining a greater amount of the thread form for purposes of insuring alignment of the threads during insertion into the disc space. However, a trade off of the smaller amount of concavity into side walls 222 and 224 is that, in comparison to the embodiment of FIG. 1, a pair of fusion devices according to the embodiment of FIG. 8 will have an increased width when placed within the disc space.

Figure 9:
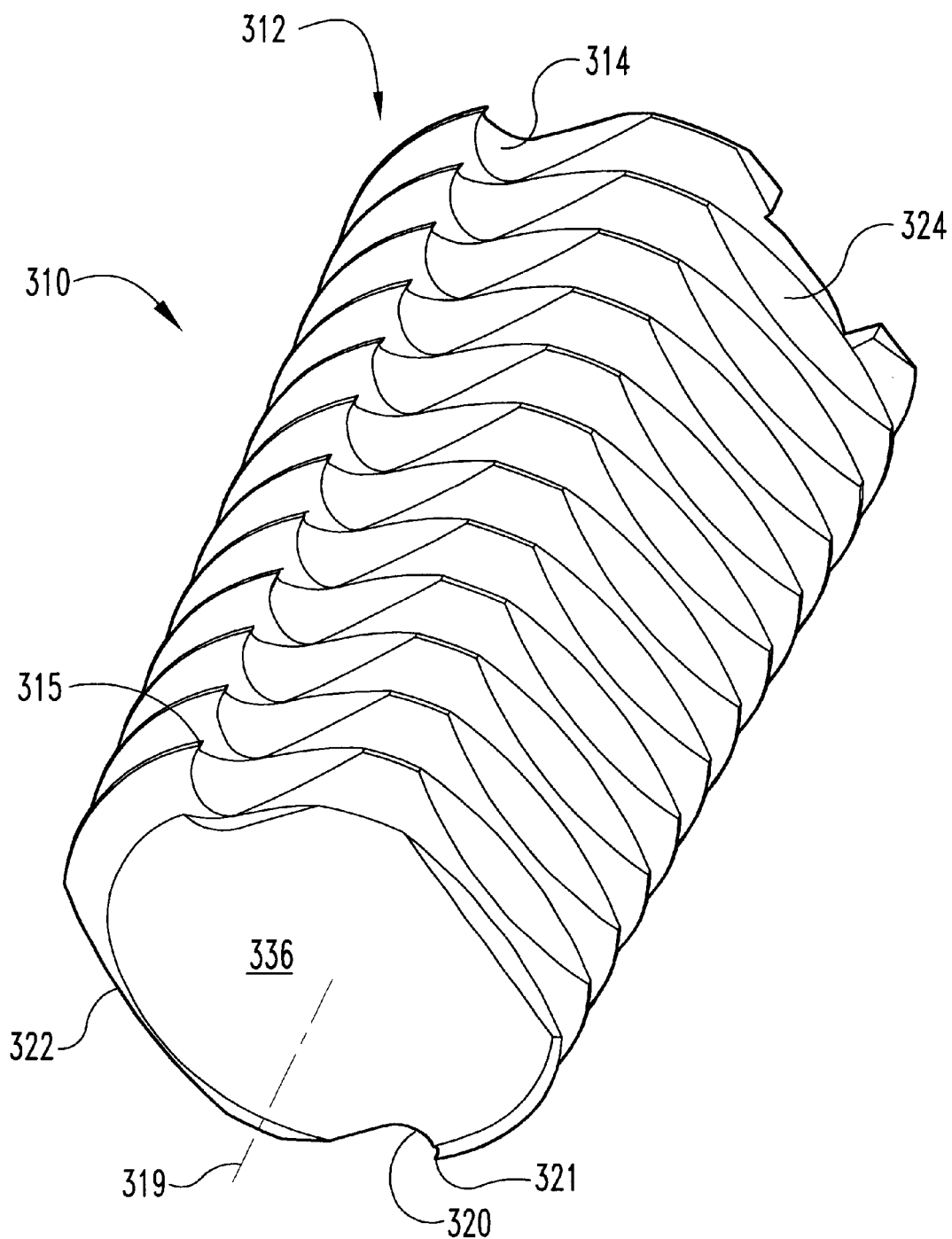
FIG. 9 is a perspective view of a fourth embodiment of an improved interbody fusion device according to the present invention.

Referring now to FIG. 9, there is shown still a further embodiment of an improved interbody fusion device according to the present invention. Interbody fusion device 310 includes a thread form 312 tapering from a smaller diameter thread form adjacent distal end 336 to a larger diameter thread form opposite end 336. However, the outer surface of fusion device 310 also includes a tapering outer surface substantially matching the taper of threads 312. Thus, the thread height is substantially constant from the distal end 336 to the opposite second end. Thread form 312 is interrupted by thread cut outs 314 and 320 to form barbs 315 and 321, respectively. Thread cut outs 314 and 320 do not extend parallel to longitudinal axis 319, but instead follow the outer taper of the thread crest diameter. In contrast to the previous embodiments, opposing sidewalls 322 and 324 are substantially flat and lack concavity necessary to rotate one adjacent device within the maximum root diameter of the other. However, it is contemplated that in some applications substantially flat sidewalls 322 and 324 may be positioned adjacent the vertebral end plates and the device urged into the disc space to the desired depth without rotation. Once the desired depth has been reached, fusion device 310 may then be rotated to engage thread pattern 312 with the bone of the adjacent vertebral bodies and thereby anchor the device. Moreover, while not shown, it is contemplated that fusion device 310 may include one or more fusion windows formed through the threads or in the valleys between adjacent threads to communicate with a hollow interior.

Figure 10:
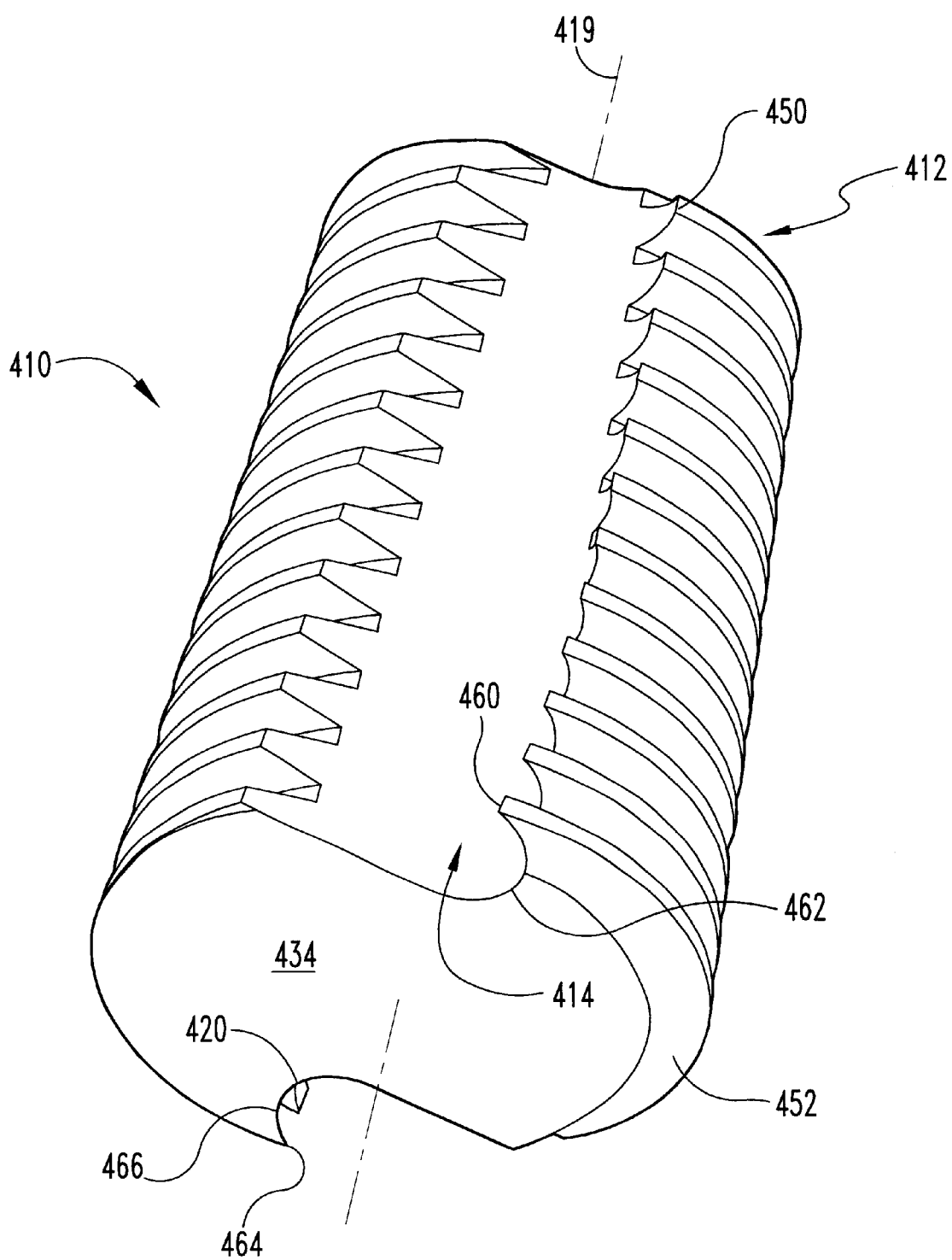
FIG. 10 is a perspective view of a fifth embodiment of an improved interbody fusion device according to the present invention.

FIG. 10 shows yet a further embodiment of an improved interbody fusion device 410 according to the present invention. Interbody fusion device 410 includes a thread pattern 412 decreasing in thread height from proximal end 434 to the opposite end of the fusion device 410. Thread form 412 is interrupted by thread cut outs 414 and 420. The thread cut outs 414 and 420 extend between tallest thread 452 and shortest thread 450 substantially parallel to the longitudinal axis 419 and along the entire length of device 410. Thread cut outs 414 and 420 create undercuts 462 and 466, respectively. Undercuts 462 and 466 create barbs 460 and 464, respectively, adjacent proximal end 434 where the thread form is taller. At the opposite end of fusion device 410, it can be seen that cut out 414 does not result in a substantial undercut 462 since the height of the thread 450 is substantially smaller than the height of thread 452.

Figure 11:
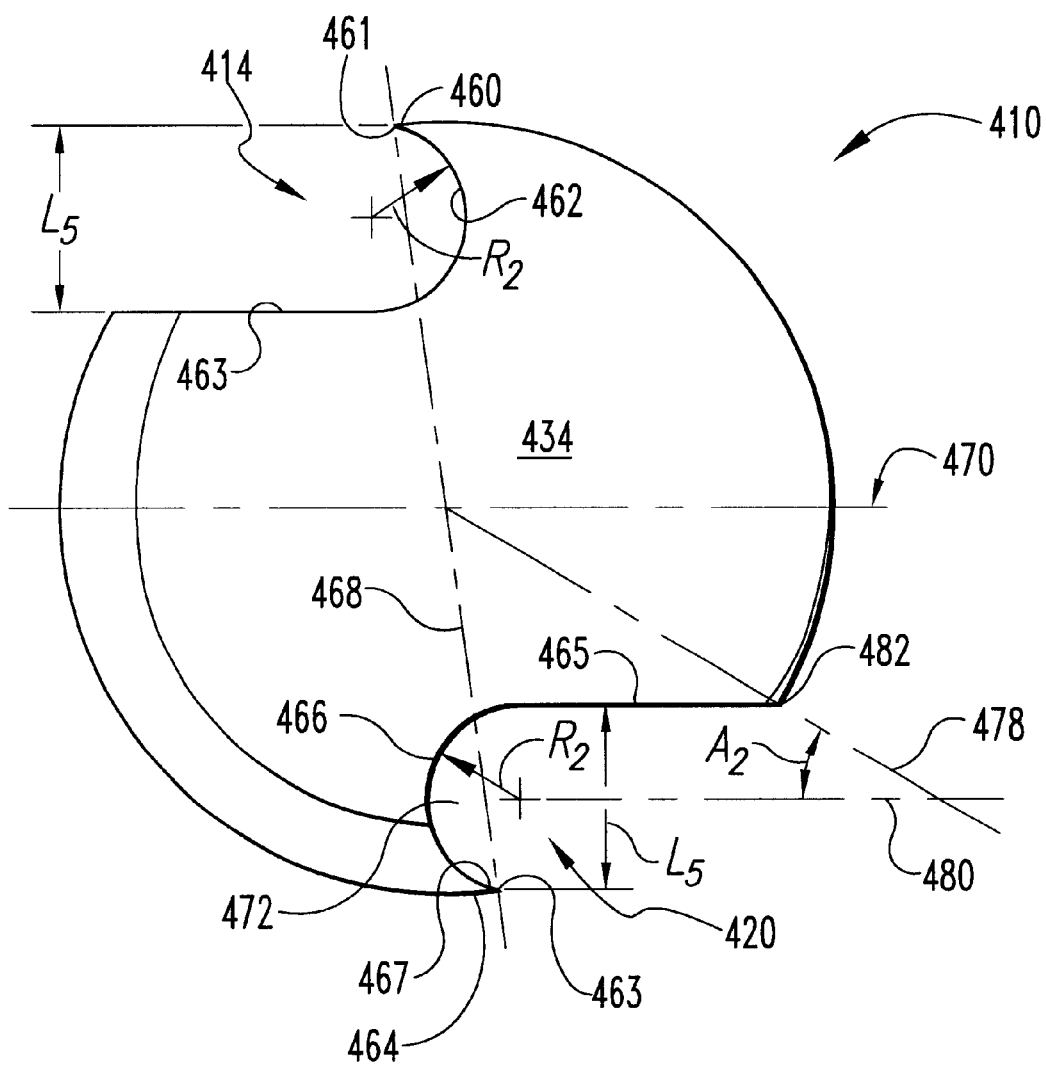
FIG. 11 is an end view of the interbody fusion device of FIG. 10.

Referring now to FIG. 11, a view of end 434 of the device of FIG. 10 is shown. Side walls 463 and 465 of cut outs 414 and 420, respectively, are in substantially parallel alignment with transverse axis 470. At thread 452, thread cut outs 414 and 420 are formed with a radius R2 resulting in thread undercut 462 and 466, respectively. While the radius R2 results in a diameter approximating 20% of the thread crest diameter. In the illustrated embodiment, radius R2 is approximately 2 mm. A smaller radius R2 will result in less material removed from the body of the device, shallower barbs, and the potential for more pronounced barbs on smaller height threads. Further, thread cut outs 414 and 420 create barbs 460 and 464 with relatively sharp points 461 and 463 where the cut out walls 463 and 465 meet the periphery of the thread form.

Thread cut out 420 has a width extending between leading wall 465 and trailing wall 467 of L5. In a preferred embodiment, L5 is approximately 4 mm. Thus, the ratio of the width or diameter of the thread cut out 420 to the diameter of device 410 is approximately 20%. However, it will be understood that this ratio may be as high as 50% or as low as single digit percentages. In further explanation of the features disclosed in FIG. 11, the centerline 480 of the thread cut out 420 is disposed at angle A2 with respect to a ray 478 extending from the center to the intersection 482 of thread cut out 420 and the thread form. It is contemplated that this angle may be less than 90° but greater than 0° to achieve a thread cut out according to the present invention. In the embodiment of FIG. 11, angle A2 is approximately 30°. Preferably, as shown in FIG. 11, a ray 468 connects thread overhang 464 with the center of the device 410. Trailing wall 467 is offset with respect to ray 468 to thereby define recess 472.

Figure 12:
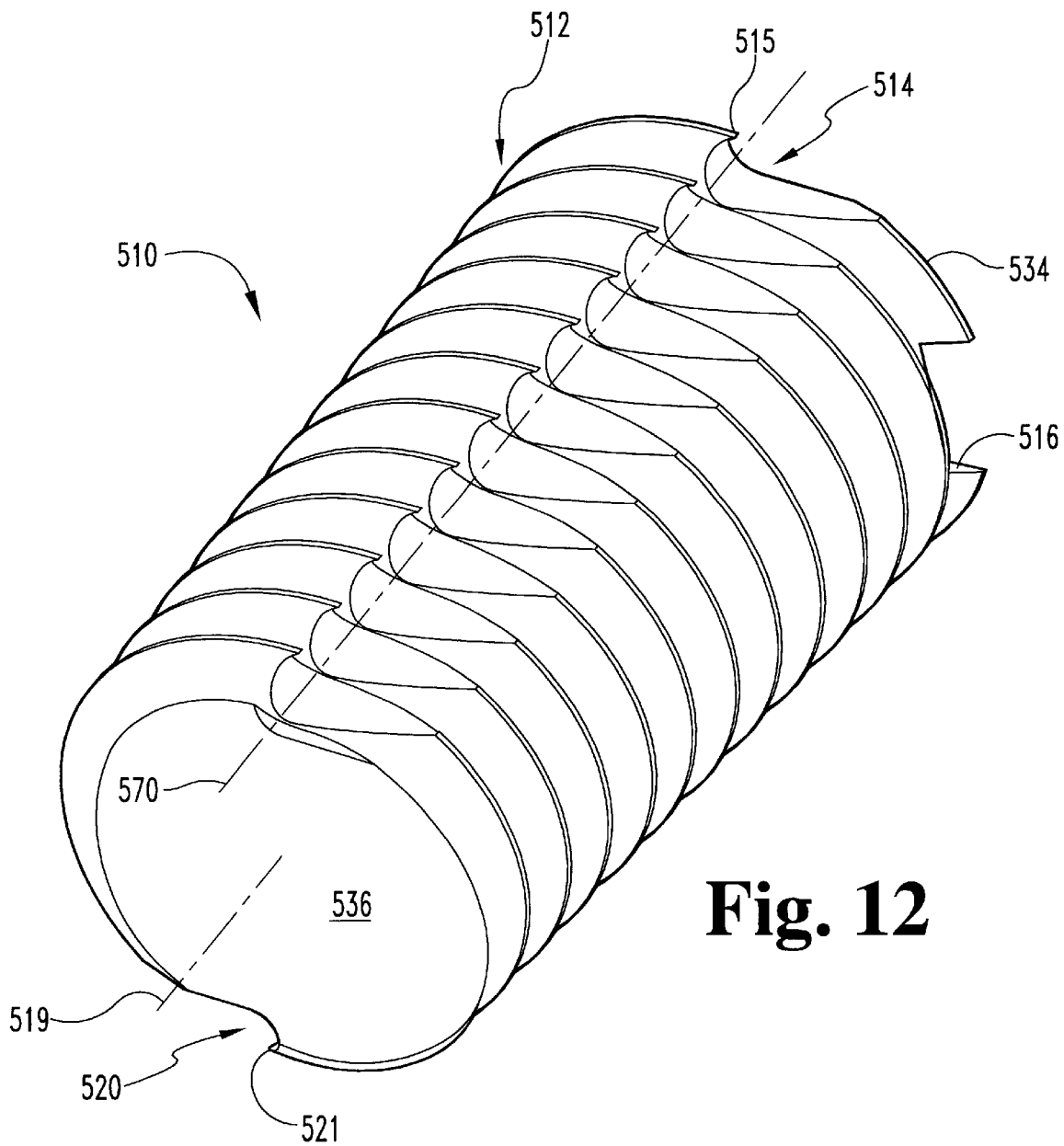
FIG. 12 is a perspective view of a sixth embodiment of an improved interbody fusion device according to the present invention.

A further embodiment of the present invention is shown in FIG. 12. Fusion device 510 includes a thread form 512 having a substantially constant thread crest height. In this embodiment, the overall diameter of the thread increases from a smaller threaded diameter adjacent distal end 536 to a larger maximum thread diameter adjacent proximal end 534. The root diameter of the device also substantially increases between the distal and proximal ends. Thread 512 is interrupted by thread cut outs 514 and 520 forming barbs 515 and 521, respectively. Thread cut outs 514 and 520 are formed along line 570, which runs substantially parallel to the tapering root diameter of the device and out of alignment with longitudinal axis 519. On proximal end 534 a portion of tool engaging slot 516 is shown.

Figure 13:
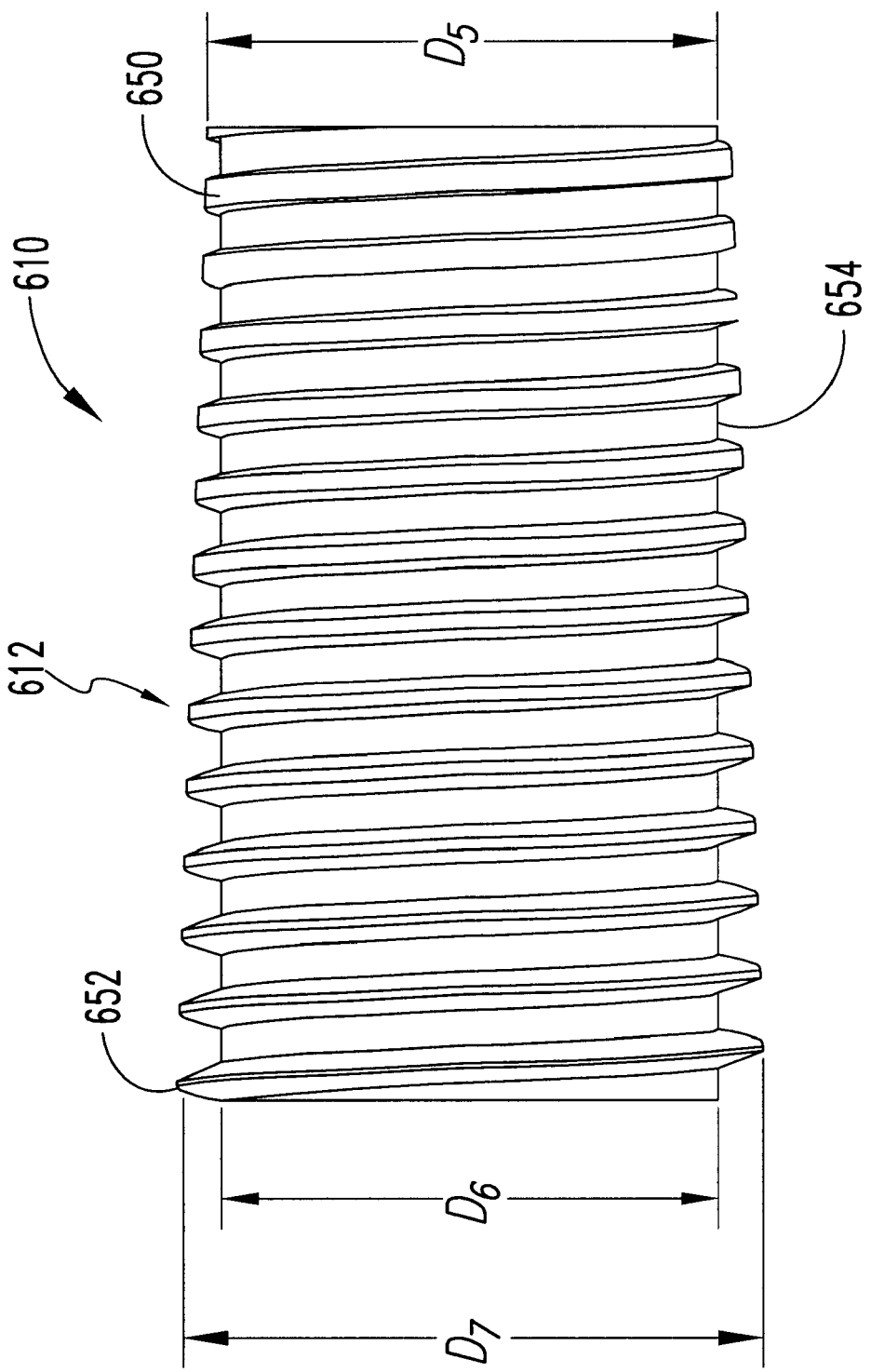
FIG. 13 is a side view of a seventh embodiment an improved interbody fusion device according to the present invention.

Referring now to FIG. 13, there is shown still another embodiment of an improved interbody fusion device 610 according to the present invention. Fusion device 610 includes an external thread pattern 612 tapering from a relatively small diameter thread form 650 to a larger diameter thread form 652. The outer surface 654 of device 610 has a diameter D6 which remains substantially constant along the entire length of the device 610. Thread form 650 has a diameter D5 that is greater than diameter D6 but less than the diameter D7 of thread form 652. The intervening thread forms substantially and continuously taper between diameters D5 and D7.

Devices according to the present invention may be formed of any suitable biocompatible material. Such materials may include, for example but without limitation, steel, titanium, tantalum, bone, composites, ceramics, plastics and the like. Furthermore, devices incorporating the present invention may be hollow, solid or formed of porous material. Moreover, while thread cut outs have been shown extending along the length of the device to create a longitudinally extending series of barbs, it is contemplated that cut outs may be placed in one or more threads to create one or more barbs positioned at various locations on the device. It will further be understood that while cutouts have been shown in a substantially linear form along the length of the device, cut outs may be created in the threads at alternating intervals.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A fusion device for introduction in the space between adjacent vertebrae, comprising:

an elongated body formed of a biocompatible material having a proximal end, a distal end, a longitudinal axis, and an outer surface defining a constant diameter extending between said proximal and said distal ends;

means adapted to engage an insertion tool;

a thread pattern having at least one external thread formed on said outer surface, and said at least one external thread includes a thread crest having a height and a width, and said thread pattern defining an advancing rotation direction from said distal end to said proximal end, wherein said thread pattern includes a first thread turn adjacent said proximal end, said first thread turn having a first height, and a second thread turn adjacent said distal end, said second thread turn having a second height, said first height being larger than said second height, and wherein said thread pattern includes a taper between said first thread turn and said second thread turn;

a pair of substantially similar thread cut outs on said at least one external thread and located on diametrically opposite side of said elongated body and extending substantially parallel to said longitudinal axis of said body, each of said thread cut outs forming a barb and an undercut, said undercut barb facing away from said advancing rotation direction, wherein said elongated body further includes opposing concave side walls interrupting said thread pattern and extending from substantially said proximal end to said distal end, said opposing concave side walls having a radius of curvature substantially equal to a maximum diameter of said fusion device.

2. The fusion device of claim 1, wherein said thread cut outs intersect said thread pattern at an angular offset along said advancing rotation direction with respect to an axis which dissects said concave side walls, said angular offset ranges from 0° to less than 90°.

3. The fusion device of claim 1, further including a hollow interior chamber.

4. The fusion device of claim 1, further including upper, lower and lateral bone ingrowth windows.

5. The fusion device of claim 1, further including openings cut along said thread cutouts.

6. The fusion device of claim 1 wherein said thread cut outs are substantially parallel to said outer surface of said elongated body.

7. The fusion device of claim 1, further including an interior cavity adapted to receive bone growth-promoting material, and at least one bone ingrowth window disposed through at least one of said pair of thread cut outs of said elongated body thereby allowing communication of said bone growth promoting material placed in said interior cavity with surrounding bones.

8. A fusion cage for insertion in spinal column comprising:

an elongated body having an outer surface extending along a longitudinal axis from a first end to a second end, said outer surface including two opposing concave segments and two opposing convex segments, said opposing concave and convex segments extending between said first end and said second end;

an external thread pattern defined on said opposing convex segments having a first thread form adjacent said first end, said first thread form having a first height, and a second thread form adjacent said second end, said second thread form having a second height larger than said first height, wherein said thread pattern includes a taper between said first thread form and said second thread form, and said thread pattern defining an advancing rotation direction from said second end to said first end; and a thread cut out interrupting at least one thread form on said convex segment, and forming a thread overhang and an undercut, said thread overhang faces away from said advancing direction, wherein said external thread pattern defines a first diameter and said thread cut out includes a second diameter substantially less than said first diameter and wherein said thread cut out is formed at an angle of less than 45° with respect to a ray intersecting an intersection between said external thread and said thread cut out.

9. The fusion cage of claim 8, wherein said angle is substantially 30°.

10. The fusion cage of claim 8, wherein said thread cut out has a substantially arcuate configuration.

11. The fusion cage of claim 10, wherein said arcuate configuration forms a concave portion on said trailing portion of said thread.

12. The fusion cage of claim 8, wherein said thread cut out includes a portion of said thread and a portion of said body.

13. The fusion cage of claim 8, wherein said external thread pattern includes multiple thread turns and said thread cut out removes a successively larger portion of said thread turns as the cut out extends from a proximal end to a distal end.

14. The fusion cage of claim 8, wherein said second diameter is less than half said first diameter.

15. The fusion cage of claim 8, wherein said second diameter is less than 25% of said first diameter.

16. The fusion cage of claim 8, wherein said second diameter is less than 10% of said first diameter.

17. The fusion cage of claim 8, wherein said thread cut out defines a leading edge, an opposite trailing edge, a thread overhang, and a recess.

18. The fusion cage of claim 17, wherein said elongated body includes a longitudinal axis and a ray extending between said longitudinal axis and said thread overhang, said recess being offset from said ray.

* * * * *